(12) United States Patent
Laurito

(10) Patent No.: US 11,234,735 B2
(45) Date of Patent: Feb. 1, 2022

(54) TISSUE RESECTING INSTRUMENT INCLUDING VARIABLE DRIVE

(71) Applicant: COVIDIEN LP, Mansfield, MA (US)

(72) Inventor: Tyler J. Laurito, Boston, MA (US)

(73) Assignee: Covidien LP, Mansfield, MA (US)

( * ) Notice: Subject to any disclaimer, the term of this patent is extended or adjusted under 35 U.S.C. 154(b) by 177 days.

(21) Appl. No.: 16/416,617

(22) Filed: May 20, 2019

(65) Prior Publication Data

US 2020/0367933 A1  Nov. 26, 2020

(51) Int. Cl.
*A61B 17/42*   (2006.01)
*A61B 17/32*   (2006.01)

(52) U.S. Cl.
CPC ........ *A61B 17/42* (2013.01); *A61B 17/32002* (2013.01); *A61B 2017/320032* (2013.01); *A61B 2017/320064* (2013.01); *A61B 2017/4216* (2013.01); *A61B 2217/005* (2013.01)

(58) Field of Classification Search
CPC ...... A61B 17/32002; A61B 17/320016; A61B 17/42; A61B 2017/320032; A61B 2017/320024; A61B 2017/320028; A61B 2017/320064
See application file for complete search history.

(56) References Cited

U.S. PATENT DOCUMENTS

| | | | |
|---|---|---|---|
| 6,156,049 A * | 12/2000 | Lovato | A61B 1/015 604/22 |
| 9,060,760 B2 | 6/2015 | Sullivan et al. | |
| 9,107,691 B2 | 8/2015 | Fojtik | |
| 9,913,629 B1 | 3/2018 | Sullivan et al. | |
| 2004/0249307 A1* | 12/2004 | Thompson | A61B 10/0275 600/568 |
| 2015/0305765 A1 | 10/2015 | Fojtik et al. | |
| 2017/0049441 A1 | 2/2017 | Sauer et al. | |
| 2017/0105736 A1 | 4/2017 | Chen et al. | |
| 2018/0028212 A1* | 2/2018 | Akilian | A61B 17/320783 |

* cited by examiner

*Primary Examiner* — Majid Jamialahmadi
(74) *Attorney, Agent, or Firm* — Carter, DeLuca & Farrell LLP

(57) ABSTRACT

A tissue resecting instrument includes an outer shaft defining a window at a distal end portion thereof, an inner cutting shaft extending through the outer shaft and configured to translate and rotate relative to the outer shaft to cut tissue extending through the window, and a drive assembly coupled to the inner cutting shaft. Actuation of the drive assembly in a first configuration drives translation of the inner cutting shaft at a first linear speed and rotation of the inner cutting shaft at a rotational speed. Actuation of the drive assembly in a second configuration drives translation of the inner cutting shaft at a second linear speed different from the first linear speed and rotation of the inner cutting shaft at the rotational speed.

11 Claims, 3 Drawing Sheets

TISSUE RESECTING INSTRUMENT INCLUDING VARIABLE DRIVE

FIELD

The present disclosure relates generally to the field of tissue resection. In particular, the present disclosure relates to a tissue resecting instrument including variable drive.

BACKGROUND

Tissue resecting instruments are commonly used in endoscopic tissue resection procedures within an organ, such as a uterus, by inserting an endoscope (or hysteroscope) into the uterus and passing the tissue resection instrument through the endoscope (or hysteroscope) and into the uterus. With respect to such endoscopic tissue resection procedures, tissue is resected at the surgical site and suctioned proximally through the tissue resecting instrument, along with fluid at the surgical site.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue resecting instrument including an outer shaft defining a window at a distal end portion thereof, an inner cutting shaft extending through the outer shaft, and a drive assembly coupled to the inner cutting shaft. The inner cutting shaft is configured to translate and rotate relative to the outer shaft to cut tissue extending through the window. Actuation of the drive assembly in a first configuration drives translation of the inner cutting shaft at a first linear speed and rotation of the inner cutting shaft at a rotational speed. Actuation of the drive assembly in a second configuration drives translation of the inner cutting shaft at a second linear speed different from the first linear speed and rotation of the inner cutting shaft at the rotational speed.

In an aspect of the present disclosure, a rotational input is provided to the drive assembly to rotate the drive assembly. At least one coupler is engaged with the drive assembly to translate the drive assembly in response to the rotational input.

In another aspect of the present disclosure, a trigger is coupled to the drive assembly. Manual actuation of the trigger provides the rotational input to the drive assembly.

In still another aspect of the present disclosure, in the first configuration, the at least one coupler engages a first portion of the drive assembly. In the second configuration, the at least one coupler engages a second portion of the drive assembly.

In yet another aspect of the present disclosure, the at least one coupler includes a first coupler configured to selectively engage the first portion of the drive assembly and a second coupler configured to selectively engage the second portion of the drive assembly.

In still yet another aspect of the present disclosure, the first portion of the drive assembly is a first helical channel defining a first pitch and the second portion of the drive assembly is a second helical channel defining a second pitch different from the first pitch.

In another aspect of the present disclosure, the tissue resecting instrument further includes a selector assembly including at least one actuator configured to selectively engage the drive assembly in the first configuration or the second configuration.

In yet another aspect of the present disclosure, the tissue resecting instrument further includes a vacuum generator coupled to the drive assembly and the inner cutting shaft such that, during at least a portion of the actuation of the drive assembly, the vacuum generator is configured to generate vacuum to suction cut tissue through the inner cutting shaft and into the vacuum generator.

In still another aspect of the present disclosure, the tissue resecting instrument further includes a tissue collection cartridge configured to releasably engage the housing. The tissue collection cartridge defines a port configured to communicate with the vacuum generator such that, during at least a portion of the actuation of the drive assembly, the vacuum generator urges cut tissue from the vacuum generator through the port into the tissue collection cartridge.

Another tissue resecting instrument provided in accordance with aspects of the present disclosure includes an outer shaft defining a window at a distal end portion thereof, an inner cutting shaft extending through the outer shaft, a drive assembly coupled to the inner cutting shaft, and at least one coupler. The inner cutting shaft is configured to translate and rotate relative to the outer shaft to cut tissue extending through the window. The drive assembly includes a helical member defining first and second helical channels, each defining a different pitch. The at least one coupler is configured for selective receipt within the first helical channel to engage the drive assembly in a first configuration and selective receipt within the second helical channel to engage the drive assembly in a second configuration. Actuation of the drive assembly in the first configuration drives translation of the inner cutting shaft at a first linear speed and rotation of the inner cutting shaft at a rotational speed. Actuation of the drive assembly in the second configuration drives translation of the inner cutting shaft at a second linear speed different from the first linear speed and rotation of the inner cutting shaft at the rotational speed.

In an aspect of the present disclosure, the at least one coupler includes a first coupler configured for selective receipt within the first helical channel to engage the drive assembly in the first configuration and a second coupler configured for selective receipt within the second helical channel to engage the drive assembly in the second configuration.

In another aspect of the present disclosure, a selector assembly including at least one actuator is configured to selectively engage the drive assembly in the first configuration or the second configuration.

In yet another aspect of the present disclosure, a trigger is coupled to the drive assembly and configured for manual manipulation to actuate the drive assembly.

In still another aspect of the present disclosure, a vacuum generator is coupled to the drive assembly and the inner cutting shaft such that, during at least a portion of the actuation of the drive assembly, the vacuum generator is configured to generate vacuum to suction cut tissue through the inner cutting shaft and into the vacuum generator.

In still yet another aspect of the present disclosure, a tissue collection cartridge is configured to releasably engage the housing. The tissue collection cartridge defines a port configured to communicate with the vacuum generator such that, during at least a portion of the actuation of the drive assembly, the vacuum generator urges cut tissue from the vacuum generator through the port into the tissue collection cartridge.

A method of resecting tissue provided in accordance with aspects of the present disclosure includes engaging a drive assembly in one of at least a first configuration or a second configuration and actuating the drive assembly. If the drive assembly is engaged in the first configuration, actuating the drive assembly drives translation of an inner cutting shaft at a first linear speed through and relative to an outer shaft and drives rotation of the inner cutting shaft relative to the outer shaft at a rotational speed. If the drive assembly is engaged in the second configuration, on the other hand, actuating the drive assembly drives translation of the inner cutting shaft at a second linear speed through and relative to the outer shaft and drives rotation of the inner cutting shaft relative to the outer shaft at the rotational speed. The second linear speed is different from the first linear speed.

In an aspect of the present disclosure, actuating the drive assembly includes actuating a trigger coupled to the drive assembly.

In another aspect of the present disclosure, engaging the drive assembly in either the first configuration or the second configuration includes actuating a first actuator or a second actuator, respectively.

In still another aspect of the present disclosure, the method further includes activating suction through the inner cutting shaft during at least a portion of the actuation of the drive assembly.

In yet another aspect of the present disclosure, engaging the drive assembly includes engaging the drive assembly in one of at least the first configuration, the second configuration, or a third configuration. If the drive assembly is engaged in the third configuration, actuating the drive assembly drives rotation of the inner cutting shaft relative to the outer shaft at the rotational speed without translating the inner cutting shaft relative to the outer shaft.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
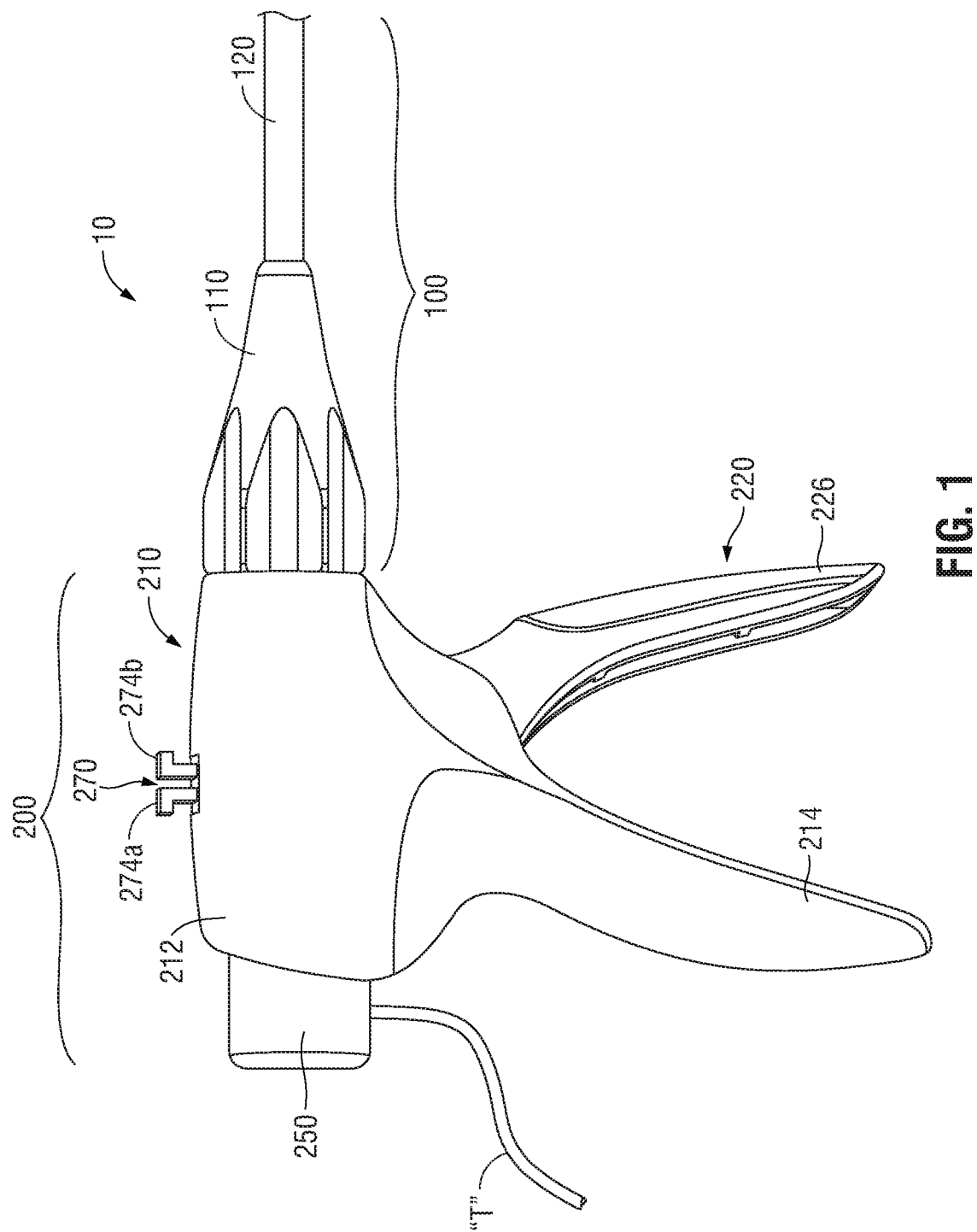
FIG. 1 is a perspective view of a proximal portion of a tissue resecting instrument provided in accordance with the present disclosure.

Referring generally to FIG. 1, a tissue resecting instrument 10 provided in accordance with the present disclosure configured for manual actuation to resect and remove tissue includes an end effector assembly 100 and a handpiece assembly 200. Tissue resecting instrument 10 may be adapted to connect to a fluid collection reservoir (not shown) via outflow tubing "T" for collecting fluid suctioned through tissue resecting instrument 10 during use or, alternatively, may be configured to internally retain the fluid suctioned therethrough, e.g., via internal outflow tubing and an internal fluid collection reservoir (not shown). As an alternative to manual actuation, tissue resecting instrument 10 may incorporate or couple to a powered drive source (not shown), e.g., a motor, for powered actuation thereof.

With continued reference to FIG. 1, tissue resecting instrument 10 may be configured as a single-use instrument that is discarded after use or sent to a manufacturer for reprocessing, a reusable instrument capable of being cleaned and/or sterilized for repeated use by the end-user, or a partially-single-use, partially-reusable instrument. With respect to partially-single-use, partially-reusable configurations, handpiece assembly 200 may be configured as a cleanable/sterilizable, reusable component, while end effector assembly 100 is configured as a single-use, disposable/reprocessable component, or vice versa. In any of the above configurations, end effector assembly 100 may be configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies 100 with handpiece assembly 200. In other embodiments, end effector assembly 100 is permanently secured to handpiece assembly 200.

Figure 2:
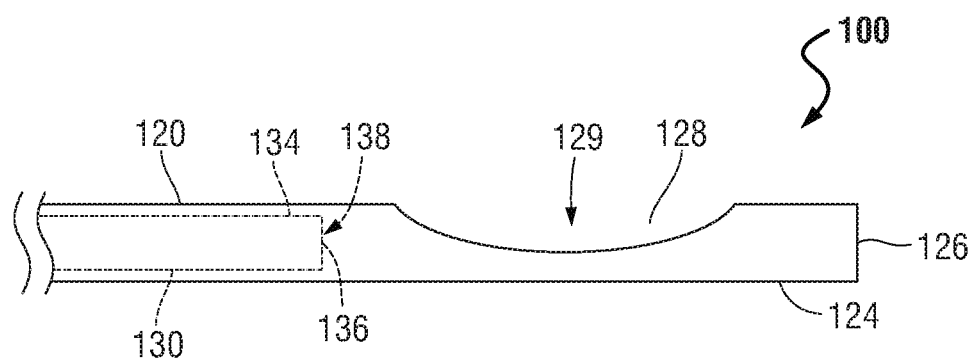
FIGS. 2 and 3 are side views of a distal portion of an end effector assembly of the tissue resecting instrument of FIG. 1 with an inner cutting shaft of the end effector assembly disposed in more-proximal and more-distal positions, respectively.
Figure 3:
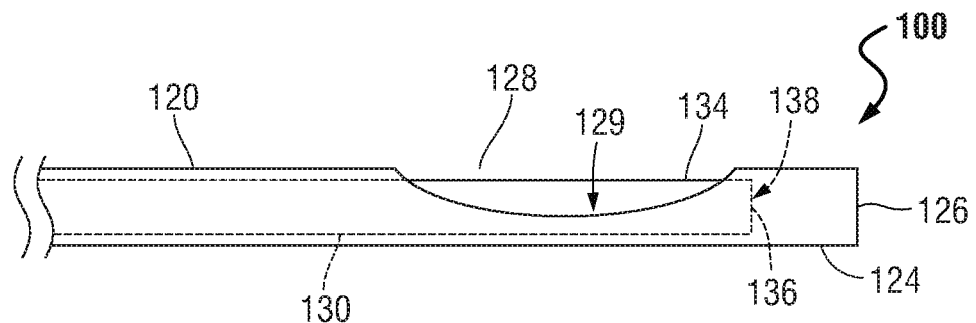
Figure 4:
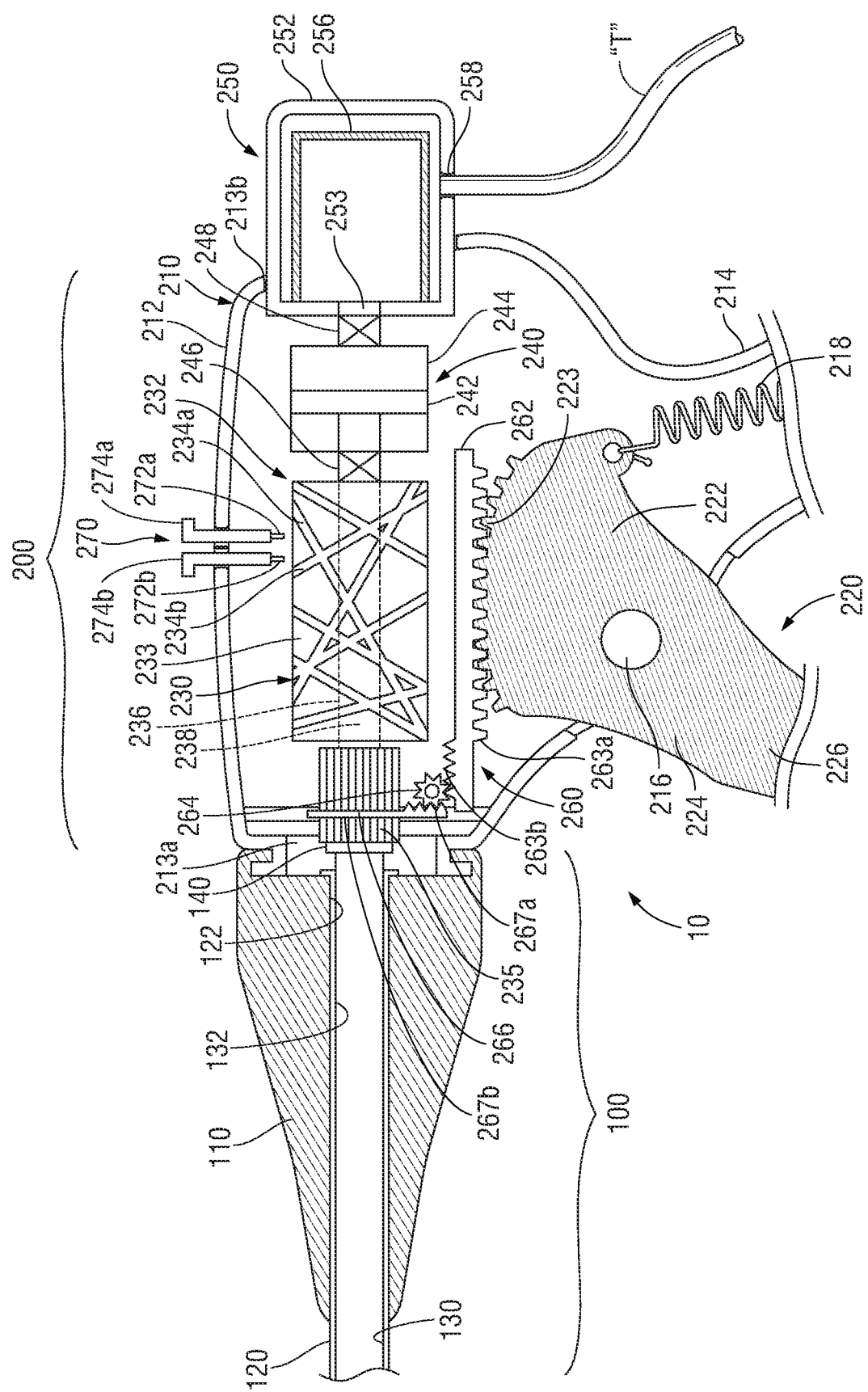
FIG. 4 is a longitudinal, cross-sectional view of the proximal portion of the tissue resecting instrument of FIG. 1.

Referring to FIGS. 2A, 2B, and 4, end effector assembly 100 includes a proximal hub housing 110 which may be formed as a rotation knob configured to rotatably engage handpiece assembly 200 (or may be configured to fixedly engage handpiece assembly 200), an outer shaft 120 fixedly engaged with and extending distally from proximal hub housing 110, an inner cutting shaft 130 movable disposed within outer shaft 120, and an inner drive hub 140 coupled to inner cutting shaft 130 such that movement imparted to inner drive hub 140, e.g., via handpiece assembly 200, as detailed below, drives translation and rotation of inner cutting shaft 130 within and relative to outer shaft 120.

Outer shaft 120 of end effector assembly 100, includes a proximal end portion 122 fixedly engaged with proximal hub housing 110. Outer shaft 120 further includes a distal end portion 124 defining a closed distal end 126 and a window 128 proximally-spaced from closed distal end 126. Window 128 provides access to the interior of outer shaft 120 and may be surrounded by a cutting edge 129 about the outer perimeter of window 128 so as to facilitate cutting of tissue passing through window 128 and into outer shaft 120.

Inner cutting shaft 130 defines a proximal end portion 132 and a distal end portion 134 defining an open distal end 136. Inner cutting shaft 130 defines an annular cutting edge 138 surrounding open distal end 136 so as to facilitate cutting of tissue passing into inner cutting shaft 130 via open distal end 136. Inner cutting shaft 130 is translatable and rotatable within and relative to outer shaft 120. More specifically, inner cutting shaft 130 is configured to translate distally and proximally in a reciprocating motion such that annular cutting edge 138 is exposed within window 128 of outer shaft 120 during at least a portion of the reciprocation motion of inner cutting shaft 130 to enable cutting of tissue extending through window 128. During the reciprocation motion of inner cutting shaft 130, inner cutting shaft 130 is further configured to rotate relative to outer shaft 120 to further facilitate cutting of tissue extending through window 128. As detailed below, suction is provided to facilitate drawing tissue into window 128 and, thus, cutting and removal of tissue through inner cutting shaft 130. Inner drive hub 140 is engaged about proximal end portion 132 of inner cutting shaft 130. In embodiments, rather than having an open distal end 136, inner cutting shaft 130 includes closed distal end and a defines a window, similarly as outer shaft 120.

Referring to FIGS. 1 and 4, handpiece assembly 200 generally includes a handle housing 210, a trigger 220 pivotably coupled to handle housing 210, a drive assembly 230 disposed within handle housing 210 and operably coupled to trigger 220, a vacuum generator 240 disposed within handle housing 210 and operably coupled to drive assembly 230, a tissue collection cartridge 250 releasably coupled to handle housing 210 (although in other embodiments tissue collection cartridge is permanently coupled to handle housing 210) and operably coupled to vacuum generator 240, and a selector assembly 270. Outflow tubing "T" couples tissue collection cartridge 250 to the fluid collection reservoir (not shown) for collecting fluid suctioned through tissue resecting instrument 10 during use. Alternatively, as noted above, handle housing 210 may include internal outflow tubing and an internal fluid collection reservoir (not shown) coupled to tissue collection cartridge 250 to retain the fluid suctioned through tissue resecting instrument 10 during use within tissue resecting instrument 10. Further, as also noted above, tissue resecting instrument 10 may be configured for powered actuation and, in such embodiments, a motor and one or more actuation buttons (not shown) replaces trigger 220. Other suitable powered or manual actuators are also contemplated.

Handle housing 210 defines a pistol-grip configuration, although other configurations are also contemplated, and includes a barrel portion 212 and a fixed handle portion 214 depending from barrel portion 212. Barrel portion 212 includes a distal port 213a about which proximal hub housing 110 of end effector assembly 100 is configured to releasably engage handle housing 210, e.g., via snap-fit engagement, with inner cutting shaft 130 and inner drive hub 140 extending through distal port 213a into handle housing 210. Barrel portion 212 also includes a proximal port 213b configured to receive (releasably or permanently) at least a portion of tissue collection cartridge 250, e.g., in threaded engagement, friction-fit engagement, etc. Barrel portion 212 of handle housing 210 houses drive assembly 230 and vacuum generator 240 therein.

Handle housing 210 supports a pivot 216 therein about which trigger 220 is pivotably coupled, thereby enabling trigger 220 to pivot relative to fixed handle portion 214 of handle housing 210 through an actuation stroke between an un-actuated position, wherein trigger 220 is further-spaced from fixed handle portion 214, and an actuated position, wherein trigger 220 is closer to fixed handle portion 214. The actuation stroke of trigger 220 includes a forward stroke portion involving movement of trigger 220 from the un-actuated position to the actuated position, and a return stroke portion, involving movement of trigger 220 from the actuated position back to the un-actuated position. Fixed handle portion 214 retains a first end (not shown) of a biasing member 218, e.g., an extension spring, in fixed position relative to fixed handle portion 214. A second end of biasing member 218 is engaged with trigger 220 such that biasing member 218 biases trigger 220 towards the un-actuated position.

Trigger 220 includes an upper drive portion 222, an intermediate pivot portion 224, and a lower manipulation portion 226, and may be formed as a single, monolithic piece or may otherwise be formed as a unitary structure. Intermediate pivot portion 224 of trigger 220 is pivotably coupled to handle housing 210 about pivot 216. Upper drive portion 222 of trigger 220 extends upwardly from intermediate pivot portion 224 into handle housing 210 to operably couple to drive assembly 230. More specifically, upper drive portion 222 defines an arcuate gear rack 223 including a plurality of gear teeth disposed on a convex side of arcuate gear rack 223. Arcuate gear rack 223 is configured to operably couple to drive assembly 230, as detailed below. Lower manipulation portion 226 of trigger 220 extends downwardly from intermediate pivot portion 224 exteriorly from handle housing 210 to enable manual manipulation thereof by a user between the un-actuated and actuated positions.

Drive assembly 230 of handpiece assembly 200 includes a helical member 232, an elongated gear 235, an inner shaft 236, and a transition gear assembly 260. Helical member 232 and elongated gear 235 are both engaged about inner shaft 236 and may abut one another or be spaced-apart from one another. Inner shaft 236 defines a lumen 238 extending therethrough. Transition gear assembly 260 operably couples arcuate gear rack 223 of trigger 220 with elongated gear 235 of drive assembly 230 such that, as detailed below, pivoting of trigger 220 about pivot 216 between the un-actuated and actuated positions drives rotation of elongated gear 234 and, thus, helical member 232.

Helical member 232 includes a cylindrical body 233 and plurality helical channels 234a, 234b (two helical channels 234a, 234b are illustrated; however additional helical channels 234a, 234b are also contemplated) defined within the exterior surface of cylindrical body 233. Each helical channel 234a, 234b defines a different pitch. Helical channels 234a, 234b are configured to receive a coupler 272a, 272b, respectively, of selector assembly 270, as detailed below. With coupler 272a received within helical channel 234a and helical member 232 driven to rotate, helical member 232 is also translated at a first speed due to the coupling of coupler 272a within helical channel 234a. This first speed corresponds to the pitch of helical channel 234a. On the other hand, with coupler 272b received within helical channel 234b and helical member 232 driven to rotate, helical member 232 is also translated at a second speed due to the coupling of coupler 272b within helical channel 234b. This second speed corresponds to the pitch of helical channel 234b and is different from the first speed due to the different pitch of helical channel 234b as compared to helical channel 234a. Helical channels 234a, 234b may be configured as bi-directional channels, e.g., wherein the respective couplers 272a, 272b are configured to move along helical channels 234a, 234b, respectively in both forward and reverse directions, or may be configured as uni-direction channels, e.g., wherein the respective couplers 272a, 272b are configured to move along first portions of helical channels 234a, 234b, respectively, in the forward direction and along second portions of the helical channels 234a, 234b, respectively, in the reverse direction. Further, as an alternative to two different couplers 272a, 272b, one coupler may be configured to selectively engage either of the helical channels 234a, 234b.

Elongated gear 235, as noted above, is engaged about inner shaft 236. As such, rotation of elongated gear 235 effects rotation of inner shaft 236 and helical member 232, which is also engaged about inner shaft 236, as also noted above. Elongated gear 235 defines a cylindrical configuration including elongated gear teeth disposed annularly about the outer periphery of elongated gear 235. Each gear tooth of elongated gear 235 extends longitudinally along at least a portion of the length of elongated gear 235.

Continuing with reference to FIGS. 1 and 4, transition gear assembly 260 includes a first gear rack 262, a pinion gear 264, and a second gear rack 266. First gear rack 262 is slidably supported within handle housing 210, disposed in generally horizontal orientation, and includes a first set of gear teeth 263a disposed in meshed engagement with arcuate gear rack 223 of upper drive portion 222 of trigger 220 such that actuation of trigger 220 translates first gear rack 262. First gear rack 262 further includes a second set of gear teeth 263b. First and second sets of gear teeth 263a, 263b, respectively, may be offset 180 degrees relative to one another.

Pinion gear 264 is rotatably supported within handle housing 210 and is disposed in meshed engagement with second set of gear teeth 263b of first gear rack 262 such that translation of first gear rack 262 rotates pinion gear 264.

Second gear rack 266 is slidably supported within handle housing 210, disposed in generally vertical orientation, and includes a first set of gear teeth 267a disposed in meshed engagement with pinion gear 264 such that rotation of pinion gear 264 translates second gear rack 266. Second gear rack 266 further includes a second set of gear teeth 277b disposed in meshed engagement with the elongated gear teeth of elongated gear 235. First and second sets of gear teeth 267a, 267b, respectively, may be offset 90 degrees relative to one another.

As a result of the above-detailed configuration of transition gear assembly 260, pivoting of trigger 220 about pivot 216 and relative to handle housing 210 from the un-actuated position towards the actuated position rotates elongated gear 235 in a first direction, while return of trigger 220 from the actuated position towards the un-actuated position rotates elongated gear 235 in a second, opposite direction.

Inner drive hub 140 of end effector assembly 100 is configured to releasably engage elongated gear 235, e.g., via mechanical fastening, friction-fit engagement, magnetic coupling, etc., upon engagement of end effector assembly 100 with handpiece assembly 200 such that inner drive hub 140 is fixed relative to elongated gear 235, and such that the interior of inner cutting shaft 130 of end effector assembly 100 is disposed in fluid communication with lumen 238 of inner shaft 236. Of course, in embodiments where end effector assembly 100 is permanently secured to handpiece assembly 200, inner drive hub 140 of end effector assembly 100 is permanently engaged to elongated gear 235. With inner drive hub 140 fixed relative to elongated gear 235, rotation of elongated gear 235, e.g., in response to pivoting of trigger 220, likewise rotates inner cutting shaft 130 relative to outer shaft 120.

Selector assembly 270 is operably supported on handle housing 210 and, as noted above, includes first and second couplers 272a, 272b, respectively, configured for selective receipt within helical channels 234a, 234b, respectively, of helical member 232. Selector assembly 270 further includes first and second actuators 274a, 274b coupled to respective couplers 272a, 272b. Actuators 274a, 274b extend from handle housing 210 to enable selective manipulation thereof by a user. Each actuator 274a, 274b is selectively actuatable from a disengaged position, wherein the corresponding coupler 272a, 272b is displaced from its respective helical channel 234a, 234b, and an engaged position, wherein the corresponding coupler 272a, 272b is received within its respective helical channel 234a, 234b. Actuators 274a, 274b may be coupled to one another or integrated into a single assembly, e.g., a toggle mechanism, such that when one of the actuators 274a, 274b is disposed in the engaged position, the other actuator 274a, 274b is disposed in the disengaged position, and vice versa. Such a configuration ensures that only one of the couplers 272a, 272b is received within its respective helical channel 234a, 234b at any given time. Other configurations are also contemplated.

The engagement of one of the couplers 272a, 272b within its respective helical channel 234a, 234b, as noted above, translates helical member 232 when helical member 232 is rotated. Since inner cutting shaft 130 is fixed relative to elongated gear 235 and elongated gear 235 is fixed relative to helical member 232, such translation of helical member 232 is imparted to inner cutting shaft 130. It is noted that elongated gear 235 translates relative to second gear rack 266 when helical member 232 is translated; however, elongated gear 235 remains disposed in meshed engagement with second gear rack 266 due to the elongated configuration thereof, along engagement along at least a portion of the length thereof.

Referring still to FIGS. 1 and 4, pivoting of trigger 220 relative to handle housing 210 between the un-actuated position and the actuated position rotates inner cutting shaft 130 relative to outer shaft 120 while simultaneously translating inner cutting shaft 130 through and relative to outer shaft 120 between a more-proximal position (FIG. 2A) and a more-distal position (FIG. 2B). More specifically, during pivoting of trigger 220 from the un-actuated position to the actuated position, inner cutting shaft 130 is rotated and translated distally from the more-proximal position (FIG. 2A) to the more-distal position (FIG. 2B), while during pivoting of trigger 220 from the actuated position to the un-actuated position, inner cutting shaft 130 is rotated and translated proximally from the more-distal position (FIG. 2B) to the more-proximal position (FIG. 2A). In this manner, inner cutting shaft 130 is rotated and reciprocated in response to actuation of trigger 220 through the full actuation stroke thereof.

In embodiments, both actuators 274a, 274b may be moved to their respective disengaged positions such that neither of the couplers 272a, 272b is received within its corresponding helical channel 234a, 234b, respectively. In such configurations, inner cutting shaft 130 is only rotated (and not translated) in response to actuation of trigger 220. Inner cutting shaft 130 may be biased or otherwise retained in a suitable longitudinal position, e.g., an intermediate position between the more-proximal position (FIG. 2A) and the more-distal position (FIG. 2B), in such configurations to facilitate cutting of tissue upon rotation of inner cutting shaft 130. As detailed above, end effector assembly 100 may be universal; however, in other embodiments, different end effector assemblies may be utilized when only rotation is desired as compared to when both rotation and reciprocation are desired.

As illustrated in FIG. 4, vacuum generator 240 is disposed within handle housing 210 and operably coupled to drive assembly 230. Vacuum generator 240 includes a chamber 244 that is disposed in fluid communication with lumen 238 of inner shaft 236 of drive assembly 230 which, as noted above, is disposed in fluid communication with the interior of inner cutting shaft 130 of end effector assembly 100. As a result, vacuum generated by vacuum generator 240 suctions tissue and fluid through window 128 of outer shaft 120, open distal end 136 of inner cutting shaft 130, lumen 238 of inner shaft 236 of drive assembly 230, and into chamber 244 of vacuum generator 240.

Vacuum generator 240, more specifically, includes a plunger 242 sealingly engaged and slidably disposed within chamber 244. In embodiments, inner shaft 236 defines the push-rod of plunger 242, although other configurations are also contemplated. Plunger 242 is coupled with helical member 232, e.g., via inner shaft 236 or in any other suitable manner, such that as helical member 232 is translated through handle housing 210, plunger 242 is similarly translated through chamber 244. More specifically, when helical member 232 is translated distally, e.g., in response to movement of trigger 220 from the un-actuated position towards the actuated position to rotate and move inner cutting shaft 130 from the more-proximal position (FIG. 2A) towards the more-distal position (FIG. 2B), plunger 242 is moved distally through chamber 244 to increase the volume of chamber 244 and generate vacuum within chamber 244, thereby establishing suction through lumen 238 of inner shaft 236 and inner cutting shaft 130. In this manner, as inner cutting shaft 130 is rotated and moved from the more-proximal position (FIG. 2A) towards the more-distal position (FIG. 2B), tissue and fluid are suctioned through window 128 of outer shaft 120, tissue is cut by open distal end 136 of inner cutting shaft 130, and the cut tissue and fluid are suctioned proximally through lumen 238 of inner shaft 236 of drive assembly 230 and into chamber 244 of vacuum generator 240.

When helical member 232 is returned proximally, e.g., in response to movement of trigger 220 from the actuated position back towards the un-actuated position to rotate and move inner cutting shaft 130 from the more-distal position (FIG. 2B) back towards the more-proximal position (FIG. 2A), plunger 242 is moved proximally through chamber 244 to push tissue and fluid, under pressure, from chamber 244 of vacuum generator 240 into tissue collection cartridge 250. One-way valves 246, 248 are disposed between vacuum generator 240 and drive assembly 230 and between vacuum generator 240 and tissue collection cartridge 250, respectively, to inhibit pumping tissue and fluid distally from vacuum generator 240 into lumen 238 of inner shaft 236 and drawing tissue and fluid distally from tissue collection cartridge 250 back into vacuum generator 240, respectively.

Other suitable vacuum generators disposed within handle housing 210, both manually-actuated and powered, may alternatively be utilized. In other embodiments, rather than providing vacuum generator 240 within handle housing 210, handpiece assembly 200 is configured to connect to a remote vacuum source (not shown) for providing suction through inner cutting shaft 130.

Tissue collection cartridge 250, as noted above, is releasably coupled to handle housing 210. Tissue collection cartridge 250, more specifically, may be configured to releasably engage proximal port 213b of handle housing 210 via threaded engagement or other suitable engagement. Tissue collection cartridge 250 includes an outer housing 252 defining a distal port 253 configured to couple, in fluid communication, with chamber 244 of vacuum generator 240 upon engagement of tissue collection cartridge 250 with handle housing 210. In this manner, tissue and fluid suctioned through window 128 of outer shaft 120, open distal end 136 of inner cutting shaft 130, lumen 238 of inner shaft 236 of drive assembly 230, and into chamber 244 of vacuum generator 240, may then be urged into tissue collection cartridge 250. One-way valve 248, as an alternative to being part of vacuum generator 240, may be disposed within distal port 253 of tissue collection cartridge 250.

Tissue collection cartridge 250 further includes an internal filter 256 disposed within outer housing 252 that is configured to permit passage of fluid therethrough but inhibit the passage of tissue therethrough. An outflow port 258 configured to enable connection of outflow tubing "T" with tissue collection cartridge 250 enables the fluid that passes through filter 256 to drain out from tissue collection cartridge 250 to a fluid collection reservoir (not shown).

In embodiments, rather than providing tissue collection cartridge 250, outflow tubing "T" is coupled to vacuum generator 240 and tissue and fluid are urged therethrough to a collection reservoir (not shown). In other embodiments, neither tissue collection cartridge 250 nor vacuum generator 240 are provided and outflow tubing "T" is coupled to drive assembly 230 at one end and to a vacuum/collection assembly at a second end to suction tissue and fluid from inner cutting shaft 130 to the collection reservoir (not shown).

Referring generally to FIGS. 1-2B and 4, in preparation for use, if not already done so, end effector assembly 100 is engaged with handpiece assembly 200, tissue collection cartridge 250 is engaged with handle housing 210 of handpiece assembly 200, and outflow tubing "T" is coupled between tissue collection cartridge 250 and the fluid collection reservoir (not shown). In embodiments, any or all of the above engagements and/or couplings are accomplished during manufacturing and, thus, need not be performed by the end-user. Further, depending upon the desired speed of translation of inner cutting shaft 130, either actuator 274a is moved to the engaged position or actuator 274b is moved to the engaged position to position coupler 272a within helical channel 234a or to position coupler 272b within helical channel 234b, respectively.

With tissue resecting instrument 10 assembled as detailed above, in use, tissue resecting instrument 10 is inserted into an internal body cavity or organ, e.g., a uterus, such that the distal end portion of end effector assembly 100 is positioned adjacent tissue to be removed. Tissue resecting instrument 10 may be inserted through an endoscope, e.g., a hysteroscope, or other instrument, or may be used independently. Once tissue resecting instrument 10 is positioned as desired adjacent tissue to be removed, tissue resecting instrument 10 is activated by pivoting trigger 220 relative to fixed handle portion 214 of handle housing 210 through the actuation stroke from the un-actuated position to the actuated position and back to the un-actuated position to thereby rotate and reciprocate inner cutting shaft 130 through and relative to outer shaft 120 (e.g., from the more-proximal position (FIG. 2A) to the more-distal position (FIG. 2B) and back to the more-proximal position (FIG. 2A)), suction cut tissue and fluid through inner cutting shaft 130 and lumen 238 of inner shaft 236 into vacuum generator 240, and urge tissue and fluid from vacuum generator 240 into tissue collection cartridge 250. Tissue resecting instrument 10 may be repeatedly actuated as detailed above to cut and remove target tissue as desired. If desired, a different actuator 274a, 274b may be moved to the engaged position to enable different cutting speeds for different actuations during use, e.g., depending upon the tissue to be cut, how much suction is desired during an actuation, etc. The rotation speed of inner cutting shaft 130 remains constant regardless of the translation speed of inner cutting shaft 130.

Tissue urged into tissue collection cartridge 250 during use is retained therein, while the fluid urged into tissue collection cartridge 250 passes through filter 256, outflow port 258, and outflow tubing "T" to the fluid collection reservoir (not shown).

Once the desired tissue is removed, tissue resecting instrument 10 may be removed from the surgical site. Thereafter, end effector assembly 100 and tissue collection cartridge 250 may be disengaged from handpiece assembly 200. End effector assembly 100 and/or handpiece assembly 200 may then be discarded, sent for reprocessing, or sterilized for reuse. Tissue collection cartridge 250 may be sent to pathology for analyzing the tissue retained therein or may likewise be discarded.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue resecting instrument, comprising:
   an outer shaft defining a window at a distal end portion thereof;
   an inner cutting shaft extending through the outer shaft, the inner cutting shaft configured to translate and rotate relative to the outer shaft to cut tissue extending through the window; and
   a drive assembly coupled to the inner cutting shaft, wherein actuation of the drive assembly in a first configuration drives translation of the inner cutting shaft in a first direction at a first linear speed and rotation of the inner cutting shaft at a rotational speed, and wherein actuation of the drive assembly in a second configuration drives translation of the inner cutting shaft in the first direction at a second linear speed different from the first linear speed and rotation of the inner cutting shaft at the rotational speed;
   wherein a rotational input is provided to the drive assembly to rotate the drive assembly, and wherein at least one coupler engaged with the drive assembly translates the drive assembly in response to the rotational input;
   wherein, in the first configuration, the at least one coupler engages a first portion of the drive assembly, and wherein, in the second configuration, the at least one coupler engages a second portion of the drive assembly; and
   wherein the at least one coupler includes a first coupler configured to selectively engage the first portion of the drive assembly and a second coupler configured to selectively engage the second portion of the drive assembly.

2. The tissue resecting instrument according to claim 1, further comprising a trigger coupled to the drive assembly, wherein manual actuation of the trigger provides the rotational input to the drive assembly.

3. The tissue resecting instrument according to claim 1, wherein the first portion of the drive assembly is a first helical channel defining a first pitch and wherein the second portion of the drive assembly is a second helical channel defining a second pitch different from the first pitch.

4. The tissue resecting instrument according to claim 1, further comprising:
   a vacuum generator coupled to the drive assembly and the inner cutting shaft such that, during at least a portion of the actuation of the drive assembly, the vacuum generator is configured to generate vacuum to suction cut tissue through the inner cutting shaft and into the vacuum generator.

5. The tissue resecting instrument according to claim 4, further comprising:
   a tissue collection cartridge configured to releasably engage a housing of the tissue resecting instrument, the tissue collection cartridge defining a port configured to communicate with the vacuum generator such that, during at least a portion of the actuation of the drive assembly, the vacuum generator urges cut tissue from the vacuum generator through the port into the tissue collection cartridge.

6. The tissue resecting instrument according to claim 1, wherein:
   actuation of the drive assembly in the first configuration drives reciprocation of the inner cutting shaft such that, after translation of the inner cutting shaft in the first direction at the first linear speed and rotation of the inner cutting shaft at the rotational speed, the inner cutting shaft is translated in a second direction at the first linear speed and the inner cutting shaft is rotated at the rotational speed, and
   actuation of the drive assembly in the second configuration drives reciprocation of the inner cutting shaft such that, after translation of the inner cutting shaft in the first direction at the second linear speed and rotation of the inner cutting shaft at the rotational speed, the inner cutting shaft is translated in the second direction at the second linear speed and the inner cutting shaft is rotated at the rotational speed.

7. A tissue resecting instrument, comprising:
   an outer shaft defining a window at a distal end portion thereof;
   an inner cutting shaft extending through the outer shaft, the inner cutting shaft configured to translate and rotate relative to the outer shaft to cut tissue extending through the window;
   a drive assembly coupled to the inner cutting shaft, the drive assembly including a helical member defining first and second helical channels, each of the helical channels defining a different pitch; and
   at least one coupler configured for selective receipt within the first helical channel to engage the drive assembly in a first configuration and selective receipt within the second helical channel to engage the drive assembly in a second configuration,
   wherein actuation of the drive assembly in the first configuration drives translation of the inner cutting shaft in a first direction at a first linear speed and rotation of the inner cutting shaft at a rotational speed, and wherein actuation of the drive assembly in the second configuration drives translation of the inner cutting shaft in the first direction at a second linear speed different from the first linear speed and rotation of the inner cutting shaft at the rotational speed;
   wherein the at least one coupler includes a first coupler configured for selective receipt within the first helical channel to engage the drive assembly in the first configuration and a second coupler configured for selective receipt within the second helical channel to engage the drive assembly in the second configuration.

8. The tissue resecting instrument according to claim 7, further comprising a trigger coupled to the drive assembly and configured for manual manipulation to actuate the drive assembly.

9. The tissue resecting instrument according to claim 7, further comprising:
   a vacuum generator coupled to the drive assembly and the inner cutting shaft such that, during at least a portion of the actuation of the drive assembly, the vacuum generator is configured to generate vacuum to suction cut tissue through the inner cutting shaft and into the vacuum generator.

10. The tissue resecting instrument according to claim 9, further comprising:

a tissue collection cartridge configured to releasably engage a housing of the tissue resecting instrument, the tissue collection cartridge defining a port configured to communicate with the vacuum generator such that, during at least a portion of the actuation of the drive assembly, the vacuum generator urges cut tissue from the vacuum generator through the port into the tissue collection cartridge.

11. The tissue resecting instrument according to claim 7, wherein:

actuation of the drive assembly in the first configuration drives reciprocation of the inner cutting shaft such that, after translation of the inner cutting shaft in the first direction at the first linear speed and rotation of the inner cutting shaft at the rotational speed, the inner cutting shaft is translated in a second direction at the first linear speed and the inner cutting shaft is rotated at the rotational speed, and actuation of the drive assembly in the second configuration drives reciprocation of the inner cutting shaft such that, after translation of the inner cutting shaft in the first direction at the second linear speed and rotation of the inner cutting shaft at the rotational speed, the inner cutting shaft is translated in the second direction at the second linear speed and the inner cutting shaft is rotated at the rotational speed.

\* \* \* \* \*